United States Patent [19]

Honnen

[11] 3,960,515

[45] *June 1, 1976

[54] HYDROCARBYL AMINE ADDITIVES FOR DISTILLATE FUELS

[75] Inventor: Lewis R. Honnen, Petaluma, Calif.

[73] Assignee: Chevron Research Company, San Francisco, Calif.

[ * ] Notice: The portion of the term of this patent subsequent to Aug. 5, 1992, has been disclaimed.

[22] Filed: Feb. 19, 1974

[21] Appl. No.: 443,939

Related U.S. Application Data

[63] Continuation of Ser. No. 405,707, Oct. 11, 1973, Pat. No. 3,898,056, which is a continuation-in-part of Ser. No. 318,064, Dec. 26, 1972, abandoned, which is a continuation-in-part of Ser. No. 318,063, Dec. 26, 1972, abandoned.

[52] U.S. Cl. .................................. 44/58; 44/63; 44/72; 44/74; 260/268 R; 260/583 P
[51] Int. Cl.² ............................................. C10L 1/22
[58] Field of Search ............... 44/74, 72, 58, 63

[56] References Cited

UNITED STATES PATENTS

| | | | |
|---|---|---|---|
| 3,438,757 | 4/1969 | Honnen et al. | 44/72 |
| 3,671,511 | 6/1972 | Honnen et al. | 44/58 |

*Primary Examiner*—Floyd D. Higel
*Assistant Examiner*—Y. Harris-Smith
*Attorney, Agent, or Firm*—G. F. Magdeburger; C. J. Tonkin; J. Tedd Brooks

[57] ABSTRACT

A mixture of high and low molecular weight hydrocarbyl amines exhibit excellent detergency and dispersancy in fuels. The high molecular weight hydrocarbyl amine contains at least one hydrocarbyl group having a molecular weight from about 1,900 to 5,000 and the low molecular weight hydrocarbyl amine contains at least one hydrocarbyl group having a molecular weight from about 300 to 600. The weight ratio of low molecular weight amine to high molecular weight amine in the mixture is maintained between about 0.5 and 5:1.

16 Claims, No Drawings

HYDROCARBYL AMINE ADDITIVES FOR DISTILLATE FUELS

CROSS-REFERENCE TO RELATED APPLICATIONS

This application is a continuation of U.S. application Ser. No. 405,707 filed Oct. 11, 1973, now U.S. Pat. No. 3,898,056 in turn is a continuation-in-part of U.S. application Ser. No. 318,064, filed Dec. 26, 1972, now abandoned and U.S. application Ser. No. 318,063, now abandoned filed Dec. 26, 1972.

BACKGROUND OF THE INVENTION

Field of the Invention

Numerous deposit forming substances are inherent in hydrocarbon fuels. These substances when used in internal combustion engines tend to form deposits on and around constricted areas of the engine contacted by the fuel. Typical areas commonly and sometimes seriously burdened by the formation of deposits include carburetor ports, throttle body and venturies, engine intake valves, etc.

Deposits adversely affect the operation of the vehicle. For example, deposits on the carburetor throttle body and venturies increase the fuel to air ratio of the gas mixture to the combustion chamber thereby increasing the amount of unburned hydrocarbon and carbon monoxide discharged from the chamber. The high fuel-air ratio also reduces the gas mileage obtainable from the vehicle.

Deposits on the engine intake valves when they get sufficiently heavy, on the other hand, restrict the gas mixture flow into the combustion chamber. This restriction, starves the engine of air and fuel and results in a loss of power. Deposits on the valves also increase the probability of valve failure due to burning and improper valve seating. In addition, these deposits may break off and enter the combustion chamber possibly resulting in mechanical damage to the piston, piston rings, engine head, etc.

The formation of these deposits can be inhibited as well as removed by incorporating an active detergent into the fuel. Numerous fuel detergents are currently available and many are commercially employed in national brand fuels. While these detergents function to varying degrees in cleaning carburetor throttle bodies and venturies or in maintaining intake valves with reduced deposits, or in cleaning other areas such as the PCV valve, etc., only a few detergents are available to clean and maintain all of the contacted areas effectively clean. Those detergents having this property are referred to hereinafter as a broad range detergent. Those few broad range detergents available must be employed at relatively high concentrations in order to maintain their effectiveness. The employment of these high concentrations has the burdens of high costs and reduces the water tolerance properties of the fuel.

In addition to having the broad range detergent properties, it is an additional advantage of the fuel detergent to have dispersant properties. In the operation of an internal combustion engine, a small amount of the fuel additives inevitably finds access to the crankcase and admixes with the crankcase oil. The continued presence of small amounts of dispersants within the crankcase oil increase the ability of the oil to maintain sludges and the like dispersed. Thus, by developing an additive having both broad range detergency and dispersancy, those parts of the engine contacted by the fuel can be maintained effectively clean and, at the same time, those parts of the engine contacted by the crankcase oil can be maintained with reduced sludge and varnish deposits.

A class of fuel additives has recently been developed which exhibits excellent broad range detergency and good dispersancy. This class of fuel detergentdispersant additives is commonly known as the polybutene amines. Several patents disclosing the preparation and use of exemplary polybutene amines include U.S. Pat. Nos. 3,438,757; 3,565,804; 3,574,576 and 3,671,511. The polybutene amines disclosed in these patents exhibit remarkable broad range detergent-dispersant properties and their use has significantly increased the operating efficiency and has reduced the maintenance of vehicles operating on fuels containing the additive.

A problem appurtenant to the use of the polybutene amines is that of adverse economics. The additives are normally employed at a concentration between 250 and 400 parts per million for best results. Although these concentrations are relatively small, the use of the additives in gasoline fuels which are sold in vast quantities at low profits results in a substantial cost burden to the petroleum fuel suppliers. Thus, a reduction of the effective concentration of the additive to the order of 150 to 250 pers parts per million would result in a considerable economic savings.

It is therefore an object of this invention to provide a fuel additive having broad range detergent properties.

It is an additional object of this invention to provide a fuel additive having broad range detergent and dispersant properties.

It is another object of this invention to provide a fuel additive having broad range detergent properties which may be effectively employed at low concentrations.

It is another object of this invention to provide a fuel additive having broad range detergency which may be employed in fuels at low concentrations without sacrificing a loss in detergency obtained from conventional detergents.

Other objects of this invention will become apparent from the following description of the invention nd appended claims.

SUMMARY OF THE INVENTION

I have found that the aforementioned objects and their attendant advantages can be realized by incorporating into a fuel an additive comprising a mixture of high and low molecular weight hydrocarbyl amines. The high molecular weight hydrocarbyl amines contain at least one hydrocarbyl group having a molecular weight between about 1,900 and 5,000. These amines may be conveniently prepared by reacting a hydrocarbyl halide having a molecular weight between about 1,900 and 5,000 in the hydrocarbyl portion with a mono- or polyamine having from 1 to 10 amine nitrogens and from 2 to 40 carbons with a carbon to nitrogen atomic ratio between about 1 and 10:1. The low molecular weight hydrocarbyl amines contain at least one hydrocarbyl group having a molecular weight between 300 and 600. These amines may be prepared by reacting a hydrocarbyl halide having a molecular weight between about 300 and 600 in the hydrocarbyl portion with a mono- or polyamine having from 1 to 10 amine nitrogens and from 2 to 40 carbons with a carbon to nitrogen atomic ratio between about 1 and 10:1.

The weight ratio of low to high molecular weight hydrocarbyl amines must be maintained between about 0.5 and 5:1, although a ratio of 1 to 3:1 is preferred.

While the exact mechanism of the combination of high and low molecular weight hydrocarbyl amines in effecting superior broad range detergency and dispersancy is not completely understood, I have found that the particular combination exhibits substantially the same excellent detergency properties as the prior art polybutene amine detergents at a substantially lower concentration. In some areas, the instant combination exceeds the detergency of the prior art materials even when employed at the lower concentrations. Thus, the present invention is an advancement in the automotive fuel additive area and represents signficant economic advantages.

DETAILED DESCRIPTION OF THE INVENTION

The fuel composition of this invention contains a mixture of high and low molecular weight hydrocarbyl monoor polyamines or combinations thereof. As referred to herein, hydrocarbyl is a monovalent organic radical composed essentially, but not particularly entirely, of hydrogen and carbon and may be aliphatic, aromatic or alicyclic or combinations thereof, e.g., aralkyl, alkyl, alkylaryl, cycloalky, etc., and may be saturated or ethylenically unsaturated. The preferred hydrocarbyls are aliphatic. The high and low molecular weight amines generally, although not necessarily, have the same general structure.

Both the high molecular weight and low molecular weight hydrocarbyl amine may be conveniently prepared by reacting (1) a hydrocarbyl halide having from 1 to 5 halide atoms and less than 10 percent of the avialable sites substituted with a halogen atom with (2) a mono- or polyamine having from 1 to 10 amine nitrogens with at least 1 primary or secondary amino group and having from 2 to 40 carbon atoms with a carbon to nitrogen ratio between about 1 and 10:1. The weight ratio of low molecular weight hydrocarbyl amine to high molecular weight hydrocarbyl amine within the mixture will generally vary from 0.5 to 5:1 preferably 0.75 to 3:1 and more preferably from 1 to 3:1.

The high molecular weight hydrocarbyl halides may be prepared by numerous commercially avialable processes. In a preferred embodiment, the hydrocarbyl portion may be prepared by ionic or free radical polymerization of C2 to C6 monoolefins (when ethylene is employed it must be copolymerized with another higher olefin) to an olefin polymer having a number average molecular weight of 1,900 to 5,000, preferably from 2,500 to 4,400, more preferably from 2,600 to 3,800. Exemplary olefins which may be polymerized include ethylene, propylene, isobutylene, 1-butene, 1-pentene, 3-methyl-1-pentene, 4-methyl-1-pentene, etc., and preferably propylene and isobutylene.

The olefin polymer should have, as an average, at least 1 branch per 6 carbon atoms along the chain and preferably at least 1 branch per 4 carbons. The preferred olefins (propylene and isobutylene) have from 0.5 to 1 branch per carbon atom along the hydrocarbon chain.

While halogenating the olefin polymers is preferred, is recognized that the high mol weight hydrocarbyl halides may be prepared by halogenating lube oil fractions, paraffin waxes, etc.

The halogen may be introduced into the hydrocarbon molecule by various means known in the art. Most readily, either chlorine or bromine (halogen of atomic number 17–35) may be introduced by the free radical catalyzed halogenation of the hydrocarbon, or ionic addition to olefinic unsaturation. Various free radical catalysts may be used, such as peroxides, azo compounds, bromine, iodine, as well as light. Ionic catalysts are exemplified by ferric chloride. Methods of halogenation are well known in the art and do not require extensive exemplification or illustration here.

The amount of halogen introduced will depend on the particular hydrocarbon used, the desired amount of amine to be introduced into the molecule, the particular alkylene amine used, and the halogen used. However, the amount of halogen introduced will generally be in the range from about 1 to 5 halogen atoms per molecule, depending on the reactivity of the resulting halide. On a weight percent basis, the amount of halide will generally range from about 1 to 25, more usually from about 1 to 10.

The low molecular weight hydrocarbyl halides may be prepared by the same processes as disclosed above for the high molecular weight hydrocarbyl halides. The polymerization, however, is conducted until an olefin polymer having a number average molecular weight of 300 to 600, preferably from 300 to 550 and more preferably from 330 to 530 is prepared. The amount of halogen introduced into the olefin polymer will normally vary from 1 to 2 halogen atoms per molecule. In an alternative embodiment, the low mol weight hydrocarbons may be prepared by cracking the high mol weight hydrocarbons. The high and low molecular weight hydrocarbyl halides may be prepared simultaneously within the same reaction medium or separately and thereafter combined to form an admixture. This aspect is not critical to the practice of this invention and numerous obvious alternative procedures are available to form the mixture as claimed hereinafter.

MONO- OR POLYAMINE COMPONENT

The mono- or polyamine component embodies a broad class of amines having from 1 to 10 amine nitrogens and from 2 to 40 carbons with a carbon to nitrogen ratio between about 1 and 10:1. In most instances, the amine component is not a pure single product, but rather a mixture of compounds having a major quantity of the designated amine. For the more complicated polyamines, the compositions will be a mixture of amines having as the major product the compound indicated in the average composition and having minor amounts of analogous compounds relatively close in compositions to the dominant compounds.

It should be noted, that while I referred to the mixture of this invention as hydrocarbyl amines, it does not mean that these amines are made solely of carbon, hydrogen and amino nitrogen. For example, the compounds may contain minor amounts of oxygen, sulfur, non-amino nitrogen, etc., and may include small amounts of halogen.

The preferred mono- and polyamine components will have the following generalized chemical formula:

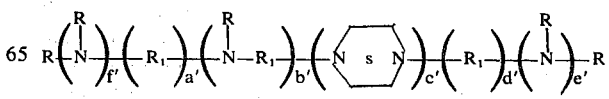

wherein

R is the same or different constituent selected from hydrogen, hydrocarbyl or hydrocarboyl having from 1 to 10 carbons and preferably aliphatic from 1 to 6 carbons, and inclusive of the mono-keto, mono-nitro, mono-hydroxy, hydrocarbonyl, alkoxy, or alkyleneoxy, derivative thereof andn preferably the mono-hydroxy or polyalkyleneoxy derivative, and at least one of said R groups is hydrogen. R1 is the same or different alkylene or hydroxy substituted alkylene having from 2 to 6 carbons and preferably from 2 to 3 carbons;

a' is an integer from 0 to 1 and preferably 1;

b' is an integer from 0 to 4 and preferably from 0 to 2;

c' is an integer from 0 to 1 and preferably 0;

d' is an integer from 0 to 1 and preferably 1;

e' is an integer from 0 to 1 and preferably 1;

f' is an integer from 0 to 1 and equal to 1 when c' is 0.

As employed herein, the recitation "the same or different" means that the same type or different group may be employed.

Exemplary R groups include alkyls such as methyl, ethyl, propyl, butyl, isobutyl, pentyl, hexyl, octyl, etc., alkenyls such as propenyl, isobutenyl, hexenyl, octenyl, etc., hydroxyalkyls, such as 2-hydroxyethyl, 3-hydroxypropyl, hydroxy-isopropyl, 4-hydroxybutyl, 8-hydroxyoctyl, etc., ketoalkyls such as 2-ketopropyl, 6-ketooctyl, etc., alkoxy and alkyleneoxy alkyls, such as ethoxyethyl, ethoxypropyl propoxyethyl, propoxypropyl, diethyleneoxyethyl, triethyleneoxyethyl, tetraethyleneoxyethyl, diethyleneoxyhexyl, diethyleneoxyoctyl, etc., acyls such as propionyl, etc. The preferred R groups are hydrogen, C1 to C6 alkyls and C1 to C6 hydroxyalkyls.

Illustrative R1 groups are ethylene, 1,2-propylene, 2,2-dimethyl propylene, trimethylene, tetramethylene, hexamethylene, etc. The preferred alkylene groups are ethylene and trimethylene.

As already indicated, in many instances a single compound will not be used as reactant in the preparation of the compositions of this invention. That is, mixtures will be used in which one or two compounds will predominate with the average composition or molecular weight as indicated. For example, tetraethylene pentamine prepared by the polmerization of aziridine or reaction of dichloroethylene and ammonia will have both lower and higher amino members, e.g., triethylene tetramine, substituted piperazine and pentaethylene hexamine, but the composition will be mainly tetraethylene pentamine and the empirical formula of the total composition will closely approximate that of tetraethylene pentamine.

The high and low molecular weight hydrocarbyl amines are readily prepared by combining the high and low molecular weight hydrocarbyl halides with the desired mono- or polyamine in the proper mol proportions. The two hydrocarbyl amine reactants may be reacted simultaneously with the amine co-reactant in the same reaction medium, or alternatively, each may be reacted with an amine in a separate reaction medium and thereafter combined to form the mixture of this invention.

The reaction or reactions may be conducted with or without the presence of a reaction solvent. A reaction solvent is generally employed whenever necessary to reduce the viscosity of the reaction product. These solvents should be stable and inert to the reactants and reaction product. Preferred solvents include aliphatic or aromatic hydrocarbons. Aliphatic alcohols may be used alone or in combination with another inert solvent.

The reaction may be carried out at room temperature (20°C), but elevated temperatures are preferred. Usually, the temperature will be in the range of from about 100° to 225°C. Depending on the temperature of the reaction, the particular halogen used, the mol ratios and the particular amine, as well as the reactant concentrations, the time may vary from 1 to 24 hours, more usually from about 2 to 10 hours. Times greatly in excess of 10 hours do not particularly enhance the yield and may lead to undesirably degradation. It is therefore preferred to limit the reaction time to fewer than 10 hours.

The mol ratio of the hydrocarbyl halides to amine will generally be in the range from about 0.2 to 20 mols of amine per mol of hydrocarbyl halide, and more usually 0.5 to 10 mols of amine per mol of hydrocarbyl halide. The mol ratio will depend upon the amount of halogen present in the hydrocarbyl halide, the particular halogen and the desired ratio of hydrocarbon to amine. If complete suppression of polysubstitution of the alkylene polyamines is desired, then large mol excesses of the amine will be used.

Small amounts of residual halogen in the final composition are not deleterious. Generally, the residual halogen as bound halogen will be in the range of 0 to 10 weight percent of the composition. Small amounts of halogen may be present as the hydrohalide salt of the hydrocarbon substituted alkylene polyamines.

After the reaction has been carried out for a sufficient length of time, the reaction mixture may be subjected to extraction with a hydrocarbon medium to free the product from any low molecular weight amine salts which have formed and any unreacted alkylene polyamines. The product may then be isolated by evaporation of the solvent. Further separation from unreacted hydrocarbyl halides and amines or purification may be carried out as desired.

Depending on the particular application of the composition of this invention, the reaction may be carried out in the medium in which it will ultimately find use, and be formed at concentrations which provide a concentrate of the detergent composition. Thus, the final mixture may be in a form to be used directly for blending in fuels.

A more detailed description of a process for preparing the hydrocarbyl amines is described in U.S. Pat. No. 3,671,511. This process may be employed in preparing the hydrocarbyl amine mixture of this invention, and the description is herein incorporated by reference.

The preferred, but not all, high and low molecular weight hydrocarbyl amines which finds use in this invention can be broadly described by the following general formula:

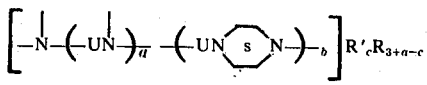

wherein

U is an alkylene having from 2 to 6 carbon atoms, there being at least 2 carbon atoms between the nitrogen atoms and preferably of from 2 to 3 carbon atoms;

a is an integer from 0 to 5, and preferably of from 0 to 4;

b is an integer from 0 to 1, preferably 0 when a is greater than 0;

a + 2b is equal to an integer between 0 and 5;

c is an integer from 1 to 4, for the average composition being in the range of about 1 to 3, on the average there being fewer R' groups than nitrogen atoms;

R is the same or different constituent selected from hydrogen or a C1 to C10 hydrocarbyl or the mono-keto, mono-nitro, monohydroxy, alkyleneoxy or alkoxy derivative thereof; and R' is a branched chain aliphatic hydrocarbon radical derived from polymerizing olefins from 2 to 6 carbon atoms, preferably from 3 to 4 carbon atoms, and more preferably from propylene and isobutylene, and having an average molecular weight in the range of 1,900 to 5,000 for the high molecular weight component and 300 to 600 for the low molecular weight component.

Illustrative compounds within the above formula are as follows: N-polyisobutenyl ethylene diamine, N-polypropenyl ethylene diamine, N-poly(1-butenyl) ethylene diamine, N-(alternating copolymer of ethylene and isobutylene) ethylene diamine (alternating copolymers of ethylene and isobutylene may be achieved by the cationic polymerization of 4-methylpentene-1), N-polypropenyl 2-aminoethylpiperazine, N-polyisobutenyl 2-aminoethylpiperazine, N-polypropenyl diethylene triamine, N-polyisobutenyl diethylene triamine, N-poly(1-pentenyl) diethylene triamine, N-polypropenyl trimethylene diamine, N-polyisobutenyl trimethylene diamine, N-polypropenyl di(trimethylene) triamine, N-polyisobutenyl di(trimethylene)triamine, N-polyisobutenyl 1,2-propylene diamine, N-polyisobutenyl di(1,2-propylene) triamine, N-polypropenyl triethylene tetramine, N-polyisobutenyl triethylene tetramine, N-(alternating copolymer of ethylene and isobutylene) triethylene tetramine, N-polypropenyl tetraethylene pentamine, N-polyisobutenyl tetraethylene pentamine, N-polyisobutenyl pentaethylene hexamine, N-polybutenyl diethanol amine, N-polyisobutenyl-N',N'-dimethylamineopropylamine; N-polybutyl, N,N'N''-trimethyl diethylene triamine, etc.

The preferred polyhydrocarbon radical substituted alkylene polyamine compositions have the following formula:

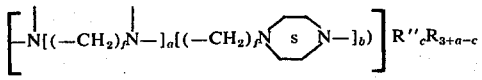

The above symbols are defined as follows:

a is an integer from 0 to 5, preferably an integer of from 0 to 4;

b is an integer from 0 to 1, preferably 0 when a is greater than 0;

a + 2b is equal to a number between 0 and 5;

c is an integer in the range of 1 to 3, on the average there being fewer R groups than nitrogen atoms;

f is an integer from 2 to 3;

R is the same or different constituent selected from hydrogen on a C1 to C10 hydrocarbyl or the mono-keto, mono-nitro, monohydroxy, alkyleneoxy or alkoxy derivative thereof; and R'' is a branched chain aliphatic hydrocarbon radical either free of or having aliphatic unsaturation, e.g., olefinic, and from 1,900 to 5,000 average molecular weight for the high molecular weight component and from 300 to about 600 average molecular weight for the low molecular weight component.

The above formulae represent broad and simplified versions of the preferred hydrocarbyl amines which may be employed in the practice of the instant invention. It should be recognized that numerous high and low molecular weight hydrocarbyl amines not defined by the above formulae may be present in minor quantities. Thus, while the above formulae define preferred hydrocarbyl amines present in major quantities, they should not be interpreted as excluding minor amounts of other components.

The mixture of hydrocarbyl amines will generally be employed in a hydrocarbon distillate fuel. The proper concentration of additive necessary in order to achieve the desired detergency and dispersancy varies depending upon the type of fuel employed, the presence of other detergents, dispersants and other additives, etc. Generally, however, from 150 to 300 weight parts per million, preferably from 150 to 250 ppm and more preferably from 175 to 250 ppm of hydrocarbyl amine mixture per part of base fuel is needed to achieve the best results. When other detergents are present, a lesser amount of hydrocarbyl amine mixture is required to a minimum of 50 parts per million. When other hydrocarbyl amines are present within the fuel composition, these amines are included in calculating the critical ratio of high and low molecular weight amines.

The detergent additive may be formulated as a concentrate, using an inert stable oleophilic organic solvent boiling in the range of about 150° to 400°F. Preferably, an aliphatic or an aromatic hydrocarbon solvent is used, such as benzene, toluene, xylene or higher boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the detergent additive. In the concentrate, the amount of the additive will be ordinarily at least 10 percent by weight and generally not exceed 70 percent by weight and preferably from 20 to 60 weight percent.

In gasoline fuels, other fuel additives may also be included such as antiknock agents, e.g., tetramethyl lead or tetraethyl lead, or other dispersants such as various substituted succinimides, etc. Also included may be lead scavengers such as aryl halides, e.g., dichlorobenzene or alkyl halides, e.g., ethylene dibromide. Additionally, anit-oxidants may be present.

A particularly useful additive is a fuel soluble carrier oil. Exemplary carrier oils include nonvolatile lubricating mineral oil, e.g., petroleum spray oil, particularly a refined naphthenic lubricating oil having a viscosity at 37.8°C (100°F) of 1,000 to 2,000 SUS. Other carrier oils which may be employed include paraffin bright stocks, or solvent refined paraffin distillate oils, having a viscosity index of 80 to 100, polyolefins such as polyisobutene, polypropylene, etc., polyalkoxy polyols and polyamines such as the Pluronics and Tetronics marketed by Wyandotte Chemical Corporation. When used, these oils are believed to act as a carrier for the detergent and assist in removing and retarding deposits. They are employed in amounts from about 0.05 to 0.5 percent by volume, based on the final gasoline composition.

The mixture of high and low molecular weight hydrocarbyl amines may also be used as dispersants and detergents in lubricating oils. Lubricating oils which may be employed include a wide variety of natural and synthetic oils such as naphthenic base, paraffin base and mixed base lubricating oils. The oils generally have a viscosity of 35 to 50,000 SUS at 37.8°C (100°F).

The following examples are presented to illustrate specific embodiments of the practice of this invention and should not be interpreted as limitations upon the scope of the invention.

EXAMPLE 1

A low molecular weight hydrocarbyl halide is prepared by charging 1,526 grams of polyisobutylene having a number average molecular weight of about 530 dissolved in 205 ml of benzene. The mixture is stirred and chlorine is introduced at a rate of about 330 ml per minute. The temperature of the reaction medium is maintained at 72°C. After the reaction mixture has taken up 137 grams of chlorine, the introduction of chlorine is terminated, the benzene solvent removed by vacuum distillation and the chlorinated polyisobutylene isolated and analyzed. Analysis reveals approximately 8.19 weight percent chlorine.

EXAMPLE 2

A high molecular weight hydrocarbyl halide is prepared by charging 5,000 grams of polyisobutylene having a molecular weight of about 2,700 dissolved in 2,300 grams of benzene. The mixture is stirred and chlorine is introduced at a rate of about 525 ml per minute. The temperature of the reaction medium is maintained at about 70°C. After about 300 minutes the reaction is terminated, the benzene solvent removed by vacuum distillation and the chlorinated polyisobutylene isolated and analyzed. Analysis reveals approximately 2.55 weight percent chlorine.

EXAMPLE 3

A high molecular weight hydrocarbyl amines is prepared by charging into a reaction vessel 2,000 grams of a 69 wt percent solution of the chlorinated polyisobutylene in benzene prepared by the method of Example 2 and 345 grams of ethylene diamine. The mixture is then heated to reflux at a temperature of 80°C and benzene allowed to distill overhead. Thereafter, the mixture is heated to 150°C for 2hours. The crude product weight 1,670 grams. The product is then washed by adding 1,670 grams of xylene and 417 grams of n-butanol, heated to reflux and 845 grams of a 3 wt percent aqueous sodium hydroxide solution added. The mixture is heated and stirred for 5 minutes at reflux and thereafter allowed to phase separate. The organic phase is recovered and washed two times with 845 grams of an aqueous 3 wt percent n-butanol solution. All of the solvents are removed by vacuum distillation and the product analyzed. An elemental analysis of the product reveals 0.79 wt percent nitrogen and a conversion to active product of 76 wt percent.

EXAMPLE 4

A low molecular weight hydrocarbyl amine is prepared by charging into a reaction vessel 1,000 grams of an 88 wt percent solution of the chlorinated polyisobutylene in benzene prepared by the method of Example 1 and 540 grams of ethylene diamine. The mixture is then heated to a temperature of 150°C allowing benzene and excess ethylene diamine to distill overhead. The temperature is maintained at 150°C for 2 hours. The resulting crude product is washed by the procedure set forth in the above Example 3. The volatile materials are stripped from the mixture by vacuum distillation. An elemental analysis of the product reveals 3.92 wt. percent nitrogen and a conversion of 87.5 percent.

EXAMPLE 5

The effectiveness of the high and low mole weight hydrocarbyl amine mixture in reducing harmful engine valve deposits is illustrated by this ASTM/CFR single-cylinder engine test. In carrying out the tests, a Waukesha CFR single-cylinder engine is used. The run is carried out for 10 hours, at the end of which time the intake valve is removed, washed with hexane and weighed. The deposits are removed with a wire brush and the valve reweighed. The differences between the two weights is the weight of the deposit with a lesser amount of deposit measured connoting a superior additive. The operating conditions of the test are as follows: water jacket temperatuer 100°C (212°F); manifold vacuum cf 15 in. Hg, intake mixture temperature of 52°C (125°F); air-fuel ratio of 14; ignition spark timing of 15° BTC; engine speed is 1,800 rpm; the crankcase oil is a commercial CHEVRON 30 W oil. The amount of carbonaceous deposit in milligrams on the intake valves is measured and reported in the following Table I.

The base fuel tested in the above extended detergency test is a regular octane gasoline containing no fuel detergent. The base fuel is admixed with varying amounts of detergent additives. Additive A is a polybutene amine prepared by reacting (1) a polyisobutene chloride having a number average molecular weight in the polyisobutene portion of about 1,400 and a chlorine content of about 4 wt. percent with (2) ethylene diamine. Additive B is a mixture of low and high molecular weight polyisobutene amines prepared by the method of Examples 3 and 4, respectively. Additive C is the same as Additive B above except that a different ratio of low to high molecular weight polyisobutene amines is employed. Each of the above fuels containing a detergent additive contains about 4parts of a carrier oil (a napthenic hydrofined pale oil with a viscosity at 37.8°C (100°F) of 1,800 SUS).

The results of the engine valve deposits tests with the above additives are presented in the following Table I.

TABLE I

INTAKE VALVE DEPOSIT TESTS

| Test | Additive | Ratio[1] | Conc. (ppm) | Valve Deposit (mg) |
|---|---|---|---|---|
| 1 | none | — | — | 90 |
| 2 | A | — | 100 | 340 |
| 3 | A | — | 150 | 100 |
| 4 | A | — | 200 | 20 |
| 5 | A | — | 250 | 22 |
| 6 | B | 1.7:1 | 100 | 325 |
| 7 | B | 1.7:1 | 150 | 85 |
| 8 | B | 1.7:1 | 200 | 20 |
| 9 | B | 1.7:1 | 250 | 15 |
| 10 | C | 2.5:1 | 100 | 320 |
| 11 | C | 2.5:1 | 150 | 30 |
| 12 | C | 2.5:1 | 200 | 8 |
| 13 | C | 2.5:1 | 250 | ≈6 |

[1]Weight ratio of low molecular weight to high molecular weight polybutene amine present in the additive.

The above table illustrates a large improvement in reduced valve deposits of Additives B and C over Additive A, particularly at a concentration of 150 ppm. At the 150 ppm concentration, Additive C illustrates a greater than 6-fold reduction in valve deposits over Additive A. Additive B illustrates a greater than 2-fold reduction over Additive A.

EXAMPLE 6

This example is presented to hypothetically illustrate several detergent-disperant mixtures of this invention. The compositions are believed to exhibit the same excellent detergency and good dispersancy properties at low concentrations. The fuel composition is composed of varying amounts of the detergent-dispersant mixture in a hydrocarbon distillate fuel boiling between about 30°C (85°F) and 216°C (420°F). Representative compositions are illustrated by the following Table II.

EXAMPLE 9

A fuel blend is prepared by admixing into a detergent-free leaded regular gasoline, 130 ppm (parts per million) of the low molecular weight hydrocarbyl-monoethanol amine prepared by the method of Example 7, 56 ppm of the high molecular weight hydrocarbyl-monoethanol amine prepared by the method of Example 8 and 1,000 ppm of a hydrocarbon carrier oil (a naphthenic lube oil having a viscosity of about 1,800 SUS at 37.8°C (100°F)). The fuel blend is tested in the Intake Valve Deposit Test as described in Example 5 to reveal a valve deposit of 38 mg.

EXAMPLE 10

A preparation of a low molecular weight dime-

TABLE II
REPRESENTATIVE COMPOSITIONS
Polybutene Amine Additive

| Composition | High Molecular Weight Type | MW[1] | Low Molecular Weight Type | MW[1] | Other Additives Type | Concentration (ppm) |
|---|---|---|---|---|---|---|
| 1 | PBEDA[2] | 2700 | PBEDA | 530 | — | — |
| 2 | PBEDA | 2700 | PBEDA | 530 | TEL[3] | 120 |
| 3 | PBEDA | 2700 | PBEDA | 530 | TEL | 170 |
| 4 | PBEDA | 2500 | PBEDA | 530 | | |
| 5 | PBEDA | 2500 | PBEDA | 440 | | |
| 6 | PBEDA | 4300 | PBEDA | 530 | | |
| 7 | PBEDA | 4300 | PBEDA | 440 | | |
| 8 | PBEDA | 4300 | PBEDA | 330 | | |
| 9 | PBDETA[4] | 2700 | PBDETA | 530 | | |
| 10 | PBTETA[5] | 2700 | PBTETA | 530 | | |
| 11 | PBTEPA[6] | 2700 | PBTEPA | 530 | | |
| 12 | PBTEPA | 2700 | PBEDA | 530 | | |
| 13 | PBDEA[7] | 2700 | PBDEA | 530 | | |

[1]Number average molecular weight of the hydrocarbon portion of the molecule.
[2]PBEDA is polybutene (PB) ethylene diamine prepared by reacting polybutene halide with ethylene diamine.
[3]Tetraethyl lead.
[4]PBDETA is polybutene diethylene triamine.
[5]PBTETA is polybutene triethylene tetraamine.
[6]PBTEPA is polybutene tetraethylene pentaamine.
[7]PBDEA is polybutene diethanol amine.

EXAMPLE 7

The preparation of a low molecular weight hydrocarbyl monoethanol amine is illustrated in this exampmle. A two-liter glass pot is charged with 200 grams of the polybutene chloride solution (12 percent benzene) prepared by the method of Example 1 and 200 grams of monoethanol amine. The contents are stirred and heated to a temperature of 150°C and maintained at that temperature for 3 hours. The crude product is washed in the same manner as described in Example 3 and the solvents removed by vacuum distillation. An elemental analysis of the product reveals 1.99 wt. percent nitrogen with a conversion to active product of 84.7 percent.

EXAMPLE 8

The preparation of a high mol weight hydrocarbyl monoethanol amine is illustrated in this example. A two-liter glass pot is charged with 880 grams of the polybutene chloride solution (31 percent benzene) preapred by the method of Example 2 and 45 grams of monoethanol amine. The contents are stirred and heated to 150°C and maintained at the temperature for 5 hours. The crude product is washed in the same manner as described in Example 3 and the solvent removed by vacuum distillation. An elemental analysis of the product reveals 0.49 wt. percent nitrogen.

thylaminopropylamine is illustrated in this example. A one-liter glass reaction vessel is charged with 200 grams of the polybutene chloride solution (12 percent benzene) prepared by the method of Example 1 and 123 grams of dimethylaminopropylamine [(CH3)2N-(CH2)3-NH2]. The contents are heated to reflux and the solvents removed until the temperature attains 150°C. The contents are maintained at a temperature between 150°–170°C for 4 hours and thereafter allowed to cool and/admixed with an equal volume of hexane. The contents are washed 3 times with 3 parts of water, one part ethanol and 0.1 part of butanol per part by volume of crude product. The solvents are stripped by vacuum distillation and a sample of the product analyzed. The base number is measured at 158 mg KOH/gram and the nitrogen content measured at 3.97 wt percent.

EXAMPLE 11

The preparation of a high molecular weight dimethylaminopropylamine is illustrated in this example. A one-liter glass reaction vessel is charged with 700 grams of the polybutene chloride solution (31 percent benzene) prepared by the method of Example 2 and 61 grams of dimethylaminopropylamine. The contents are heated to reflux and the benzene solvent removed until the temperature of the reaction medium attains 150°C. The contents are maintained at this temperature for 4 hours, thereafter cooled and admixed with an equal volume of hexane. The crude product is washed in the same manner as described in Example 10 and the solvents removed by vacuum distillation. The final product contained 0.79 wt percent nitrogen upon analysis and had a base number of 30 mg KOH/gram.

EXAMPLE 12

A fuel blend is prepared by admixing into a detergent-free regular gasoline, 214 ppm of a low molecular weight hydrocarbyl amine prepared by the method of Example 10 and 93 ppm of a high molecular weight hydrocarbyl amine prepared by the method of Example 11 along with 1,000 ppm of a carrier oil of the type employed in Example 9.

EXAMPLE 13

The preparation of a low molecular weight hydrocarbyl hydroxyethyl ethylene diamine is illustrated in this example. The reaction procedure and washing steps are the same herein as are recited for Example 10. The following amounts are employed - 200 grams of polybutene chloride solution as prepared in Example 1, 124 grams of hydroxethyl ethylene diamine [NH2-(CH2)2NH(CH2)20H]. The resulting final product has a base number of 111 mg KOH/gram and a nitrogen content of 3.29 wt percent.

EXAMPLE 14

The preparation of a high molecular weight hydrocarbyl hydroxyethyl ethylene diamine is illustrated in this example. The reaction procedure and washing steps are the same herein as are recited for Example 10. The following amounts are employed - 703 grams of polybutene chloride solution as prepared in Example 2, 62 grams of hydroxyethyl ethylene diamine. The resulting final product has a base number of 19 mg KOH/gram and a nitrogen content of 0.72 wt percent.

EXAMPLE 15

A hypothetical fuel blend is prepared by blending in a leaded premium gasoline 150 ppm of active low molecular weight hydrocarbyl amine prepared by the method of Example 13 and 50 ppm of active high molecular weight amine prepared by the method of Example 15 and 800 ppm of a polybutene carrier oil having a viscosity of about 200 SUS at 100°F.

EXAMPLE 16

The preparation of a low molecular weight hydrocarbyl diethanol amine-monoethanol amine is illustrated in this example. A 2-liter glass pot is charged with 85 grams of polybutene chloride solution (11 percent benzene) as prepared by Example 1 and 16.4 grams of diethanol amine. The contents are heated to 150°C and maintained at that temperature for 10 minutes while the benzene solvent is removed overhead. Thereafter 37.4 grams of monoethanol amine are charged to the pot and the temperature maintained at 150°C for 2 hours. The crude product is cooled and washed in accordance with the wash steps recited in Example 3. The product is analyzed and found to contain 1.78 wt percent nitrogen.

EXAMPLE 17

The hypothetical preparation of a high molecular weight hydrocarbyl diethanol amine-monoethanol amine is illustrated in this example. The reaction procedure and washing steps are the same as recited above for Example 16. The following amounts are employed: 400 grams of polybutene chloride solution as prepared by Example 2, 20.8 grams of diethanol amine and 36 grams of monoethanol amine. At the end of the washing steps, the solvents are removed by vacuum distillation.

EXAMPLE 18

A hypothetical fuel composition is prepared by blending in a blended regular gasoline, 175 ppm of active low molecular weight hydrocarbyl amine as prepared by Example 16; 75 ppm of active high molecular weight hydrocarbyl amine as prepared by Example 17 and 1,000 ppm of a carrier oil as defined in Example 9.

I claim:

1. A composition of matter comprising a mixture of a high molecular weight hydrocarbyl amines and a low molecular weight hydrocarbyl amines wherein a weight ratio of low to high molecular weight amines present within said mixture is between about 0.5 and 5:1; said high molecular weight hydrocarbyl amines being prepared by reacting a first hydrocarbyl halide having a number average molecular weight in the hydrocarbyl portion of 1,900 to 5,000 with a mono- or polyamine having from 1 to 10 amine nitrogens and from 2 to 40 carbons with a carbon to nitrogen atomic ratio between about 1 and 10:1; and said low molecular weight hydrocarbyl amines being prepared by reacting a second hydrocarbyl halide having a number average molecular weight in said second hydrocarbyl portion of 300 to 600 with a mono- or polyamine having from 1 to 10 amine nitrogens and from 2 to 40 carbons with a carbon to nitrogen atomic ratio between about 1 and 10:1.

2. The composition defined in claim 1 wherein said high and low molecular weight hydrocarbyl amines are present in an amount from 1 to 3 weight parts of low molecular weight amines per weight part of high molecular weight amines.

3. The composition defined in claim 1 wherein the molecular weight of the hydrocarbyl portion of said first hydrocarbyl halide is from 2,500 to 4,400 and wherein the molecular weight of the hydrocarbyl portion of said second hydrocarbyl halide is from 300 to 550.

4. A composition of matter comprising a mixture of high and low molecular weight hydrocarbyl amines wherein said hydrocarbyl amines are prepared by reacting a high molecular weight hydrocarbyl halide having a number average molecular weight in the hydrocarbyl portion of 2,500 to 4,400 and a low molecular weight hydrocarbyl halide having a number average molecular weight in the hydrocarbyl portion of 300 to 550 with the same or a different amine having the following general structural formula:

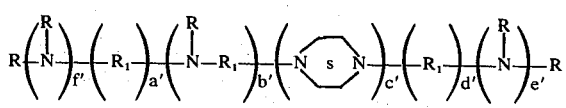

wherein
R is the same or different constituent selected from hydrogen, hydrocarbyl or the mono-keto, mononitro, mono-hydroxy, alkyleneoxy or alkoxy derivative thereof, and at least one of said R groups in said amine is hydrogen;
R1 is the same or different alkylene or hydroxy substituted alkylene having from 2 to 6 carbons;
a' is an integer from 0 to 1;

b' is an integer from 0 to 4;
c' is an integer from 0 to 1;
d' is an integer from 0 to 1;
e' is an integer from 0 to 1;
f' is an integer from 0 to 1 and equal to 1 when c' is 0. said low molecular weight hydrocarbyl amines are present in said mixture in an amount from 0.5 to 5 parts by weight per weight part of said high molecular weight hydrocarbyl amines.

5. The composition defined in claim 4 wherein said c' is zero and said high molecular hydrocarbyl halide has a number average molecular weight in the hydrocarbyl portion of 2,600 to 3,800.

6. The composition defined in claim 4 wherein said amine is ethylene diamine.

7. The composition defined in claim 5 wherein said high molecular weight hydrocarbyl halide is a hydrocarbyl chloride having a number average molecular weight in the hydrocarbyl portion of about 2,700 and wherein said low molecular weight hydrocarbyl halide is a hydrocarbyl chloride having a number average molecular weight in the hydrocarbyl portion of about 530.

8. The composition defined in claim 7 wherein said high and low molecular weight amines are present in an amount from 1 to 3 weight parts of low molecular weight amine per weight part of high molecular weight amine.

9. The composition defined in claim 8 wherein said amine is ethylene diamine.

10. A concentrate comprising an inert stable oleophilic organic solvent containing from 10 to 70 weight percent of a mixture of high and low molecular weight hydrocarbyl amines prepared by reacting a high molecular weight hydrocarbyl halide having a number average molecular weight in the hydrocarbyl portion of 1,900 to 5,000 and a low molecular weight hydrocarbyl halide having a number average molecular weight in the hydrocarbyl portion of 300 to 600 with the same or a different amine having the following general structural formula:

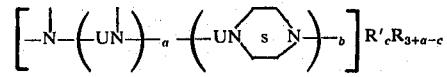

wherein R is the same or different constituent selected from
hydrogen, hydrocarbyl or hydrocarboyl having from 1 to 10 carbons or the mono-keto, mono-nitro, mono-hydroxy, alkyleneoxy or alkoxy derivative thereof, and at least one of said R groups in said amine is hydrogen;
R1 is the same or different alkylene or hydroxy substituted alkylene having from 2 to 6 carbons;
a' is an integer from 0 to 1;
b' is an integer from 0 to 4;
c' is an integer from 0 to 1;
d' is an integer from 0 to 1;
e' is an integer from 0 to 1;
f' is an integer from 0 to 1 and equal to 1 when c' is 0,
said low molecular weight hydrocarbyl amine is present in said mixture in an amount from 0.5 to 5 parts by weight per weight part of said high molecular weight hydrocarbyl amine.

11. The concentrate as defined in claim 10 wherein said high and low molecular weight amines are present in an amount from 1 to 3 weight parts of low molecular weight amine per weight part of high molecular weight amine.

12. The concentrate as defined in claim 11 wherein said high molecular weight hydrocarbyl halide is a hydrocarbyl chloride having a number average molecular weight in the hydrocarbyl portion of about 2,700 and wherein said low molecular weight hydrocarbyl halide is a hydrocarbyl chloride having a number average molecular weight in the hydrocarbyl portion of about 530.

13. The concentrate defined in claim 10 wherein the molecular weight of the hydrocarbyl portion of said high molecular weight hydrocarbyl halide is from 2,500 to 4,400 and wherein the molecular weight of the hydrocarbyl portion of said low molecular weight hydrocarbyl halide is from 300 to 550.

14. The concentrate defined in claim 10 wherein said high and low molecular weight hydrocarbyl amines have the following general formula:

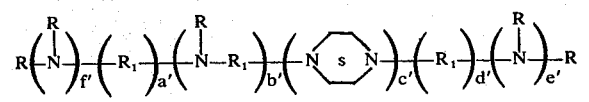

wherein
U is an alkylene having from 2 to 6 carbons;
a is an integer from 0 to 5;
b is an integer from 0 to 1;
a + 2b is equal to an integer between 0 and 5;
c is an integer from 1 to 4;
R is the same or different constituent selected from hydrogen or a C1 to C10 hydrocarbyl or the mono-keto, mon-nitro, mono-hydroxy or alkoxy derivative thereof; and
R' is a branched chain aliphatic hydrocarbon radical having an average molecular weight in the range of 2,500 to 4,400 for the high molecular weight hydrocarbyl amine and 300 to 500 for the low molecular weight hydrocarbyl amine.

15. The concentrate defined in claim 14 wherein said high molecular weight amine is polyisobutenyl ethylene diamine having an average molecular weight in the polyisobutenyl portion of 2,500 to 4,400 and said low molecular weight amine is polyisobutenyl ethylene diamine having an average molecular weight in the polyisobutenyl portion of 300 to 550.

16. A composition of matter comprising a mixture of high and low molecular weight hydrocarbyl mono- or polyamines; said high molecular weight hydrocarbyl amine containing at least one hydrocarbyl group having a molecular weight from 1,900 to 5,000 and said low molecular weight hydrocarbyl amine containing at least one hydrocarbyl group having a molecular weight from 300 to 600; the weight ratio of said low molecular weight hydrocarbyl amine to said high molecular weight hydrocarbyl amine being between about 0.5 and 5:1.

* * * * *